(12) United States Patent
Leiboff

(10) Patent No.: US 7,338,478 B2
(45) Date of Patent: Mar. 4, 2008

(54) TUBULAR APPARATUS FOR DRAINAGE OF THE COLON AND METHOD AND GUIDEWIRE FOR COLONIC INTUBATION

(76) Inventor: Arnold R. Leiboff, 5 Perigee Dr., Stony Brook, NY (US) 11790

( * ) Notice: Subject to any disclaimer, the term of this patent is extended or adjusted under 35 U.S.C. 154(b) by 351 days.

(21) Appl. No.: 10/820,518

(22) Filed: Apr. 8, 2004

(65) Prior Publication Data

US 2005/0228363 A1    Oct. 13, 2005

(51) Int. Cl.
*A61M 1/00*     (2006.01)
*A61M 5/128*    (2006.01)
*A61M 3/00*     (2006.01)
*A61M 5/44*     (2006.01)
*A61M 25/00*    (2006.01)
*A61M 31/00*    (2006.01)

(52) U.S. Cl. ............... 604/317; 604/35; 604/36; 604/44; 604/540; 604/322; 604/355; 604/528; 604/506; 604/514

(58) Field of Classification Search ............ 604/1, 604/927, 35, 36, 44, 540, 317, 332, 355, 604/528, 506, 514
See application file for complete search history.

(56) References Cited

U.S. PATENT DOCUMENTS

| | | | |
|---|---|---|---|
| 4,991,602 A * | 2/1991 | Amplatz et al. | 600/585 |
| 5,127,412 A * | 7/1992 | Cosmetto et al. | 128/898 |
| 5,545,141 A * | 8/1996 | Eld | 604/170.03 |
| 5,830,125 A * | 11/1998 | Scribner et al. | 606/139 |
| 5,851,195 A * | 12/1998 | Gill | 604/500 |
| 6,149,581 A * | 11/2000 | Klingenstein | 600/114 |
| 6,315,789 B1 * | 11/2001 | Cragg | 606/232 |

OTHER PUBLICATIONS

Online Encyclopedia, http://en.wikipedia.org/wiki/Magnus_hitch.*
J. P. Grant. Percutaneous Endoscopic Gastrostomy. Initial placement by single endoscopic technique and long-term follow-up. Ann Surg. Feb., 1993; 217(2): 168-174.*

* cited by examiner

*Primary Examiner*—Tatyana Zalukaeva
*Assistant Examiner*—Adam Marcetich
(74) *Attorney, Agent, or Firm*—Brian Roffe

(57) ABSTRACT

Method for draining and decompressing a colon in which a drainage tube is inserted through the anus into the colon to extend through the entire colon. The drainage tube is fixed in position and suction is applied therethrough to cause fecal matter to pass therein through apertures and be withdrawn from the colon. The drainage tube is inserted by inserting a guidewire into the colon through the anus, manipulating and pushing the guidewire to the cecum, passing a filament through the colon wall to engage the guidewire, pulling the guidewire out of the colon and anus to draw the filament through the colon and out of the anus, attaching the drainage tube to the filament and drawing the filament with attached drainage tube through the anus into the colon. The invention also relates to constructions of the guidewire, the drainage tube and methods for inserting drainage tubes using guidewires.

42 Claims, 10 Drawing Sheets

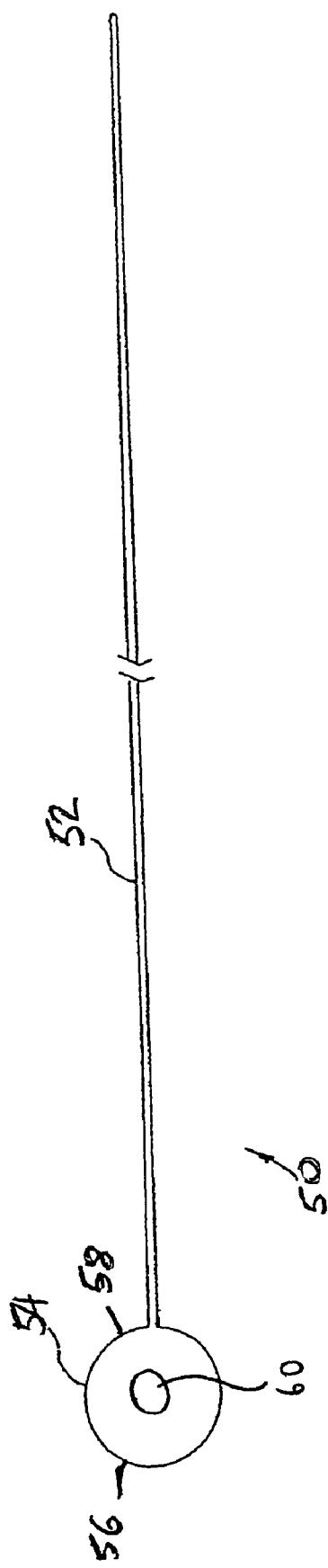
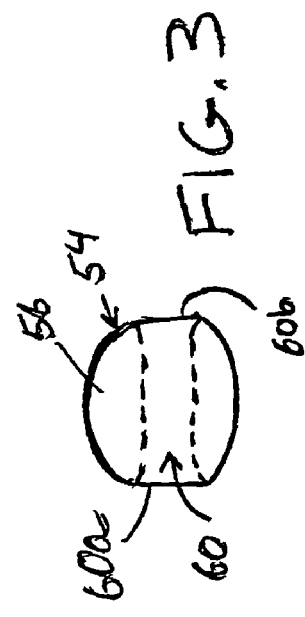

TUBULAR APPARATUS FOR DRAINAGE OF THE COLON AND METHOD AND GUIDEWIRE FOR COLONIC INTUBATION

FIELD OF THE INVENTION

The present invention relates generally to apparatus and methods for drainage of the colon and more particularly to tubular apparatus insertable into the colon for draining the colon and methods for draining the colon using such a tubular apparatus.

The present invention also relates generally to methods for inserting a tube into a colon and more specifically to methods for inserting drainage tubes into the colon which extend through the entire colon and enable the removal of enteric contents from the entire colon.

The present invention also relates generally to apparatus for aiding insertion of drainage tubes into the colon and more particularly, to guidewires for aiding insertion of drainage tubes into the colon.

The present invention also relates to methods and systems for achieving and maintaining colonic drainage and decompression in the postoperative period. For example, the invention would be used to aspirate the colon following a partial colectomy, and to divert enteric contents away from a newly created anastomosis in the colon to thereby protect the anastomosis from distension and fecal soilage and prevent or minimize anastomotic leakage and peritonitis.

BACKGROUND OF THE INVENTION

After some surgical intestinal procedures, for example, in those in which a new anastomosis is formed, it is valuable to maintain intestinal drainage and decompression, to avoid the consequences of ileus, and to safeguard the anastomosis. Various mechanisms to maintain intestinal drainage and decompression after surgery are known and include nasogastric tubes, nasointestinal tubes, cecostomy tubes, rectal tubes, obturating balloon colostomy devices and intracolonic bypass tubes. Surgical procedures and techniques are also available to maintain intestinal drainage and decompression after gastrointestinal surgery and include gastrostomies, cecostomies, ileosotomies and colostomies. There are drawbacks to each of these mechanisms and procedures.

Nasogastric tubes partially aspirate gastric contents, and to a small degree prevent distal air passage and bowel distension. However, gastric aspiration is often incomplete and succuss entericus produced by the bowel, and bacteria and gasses generated within the bowel, are not effectively evacuated. In spite of these deficiencies, nasogastric tubes are still used by many surgeons after colonic surgery, but are decreasingly popular.

While nasointestinal tubes (e.g., a Cantor Tube) may decompress the small bowel slightly better, they may not effectively prevent gastric ileus. They are usually placed preoperatively, adding to patient discomfort, and they are no more effective postoperatively than nasogastric tubes.

Cecostomy tubes and cecostomies are known to be inefficient for diversion of the fecal stream, and have been largely abandoned in favor or ileostomies or colostomies. Cecostomy tubes and cecostomies are used for colonic decompression but not for fecal diversion and have limited use postoperatively.

Ileostomies and colostomies are constructed by bringing bowel through the abdominal wall and creating an opening at skin level. Their formation is time consuming and they are fraught with complications such as abscess, hernia, prolapse and stricture. Their closure requires additional surgery. These stomas may cause intestinal obstruction. Even after temporary stomas have been closed, the adhesions which have been formed by the creation and closure of the stomas may lead to intestinal obstruction. Ileostomies and colostomies are sometimes used to protect a distal anastomosis but only when the surgeon believes that the anastomosis is particularly vulnerable to disruption.

Rectal tubes have been used to decompress the rectum, but they typically fail to divert the fecal stream away from an anastomosis and become ineffective when plugged by fecal matter. Rectal tubes are rarely used in the postoperative period.

In view of the drawbacks of the mechanisms and procedures described above, there is a need for a new technique and apparatus for decompressing the colon in the postoperative period, which is capable of effectively aspirating the colon and diverting fecal matter away from a colonic anastomosis.

OBJECTS AND SUMMARY OF THE INVENTION

It is an object of the present invention to provide new types of colonic drainage tubes for use in colonic drainage and decompression methods.

It is another object of the present invention to provide a new method for intubation of the colon to enable the colon to be drained and decompressed and to divert fecal matter away from a colonic anastomosis.

It is yet another object of the present invention to provide new guidewires for use in a colonic intubation method.

It is a still another object of the present invention to provide new techniques and systems for draining and decompressing the colon which are capable of effectively aspirating the colon and diverting fecal matter away from a colonic anastomosis.

In order to achieve these objects and others, a tubular apparatus for drainage of the colon or a drainage tube in accordance with the invention includes a flexible member having a main part defining an interior lumen or channel and a plurality of apertures leading from an outer surface to an inner surface of the member and communicating with the lumen. The member has a forward end adapted to be inserted first into the colon and a rearward end, one of these ends being connectable to a suction source. The member is fixable in place in the colon to prevent withdrawal of the member from the colon which might arise due to peristaltic movements of the colon or by inadvertent withdrawal. Suction is operatively applied to draw fecal matter from the colon into the interior lumen via the apertures and then to a waste collection device associated with the suction device.

There are various constructions of the drainage tube which differ, for example, in the manner in which a suction flow is provided. In one construction, the drainage tube includes a rearward extension portion without apertures coupled to a rearward end of the main part (that part of the drainage tube including the interior lumen and apertures in communication therewith) and having a suction channel in flow communication with the interior lumen of the main part. In this case, the suction channel is connectable to the suction source. A forward extension portion may be arranged at a forward end of the main part and defines an air inflow channel which extends through the colon wall and the abdominal wall to open to the ambient atmosphere. The forward extension portion may have a smaller cross-sectional area than the cross-sectional area of the main part and/or the interior lumen in the main part.

In another embodiment, the main part of the flexible member has both an effluent passage and a separate air passage formed alongside the effluent passage. The air passage and effluent passage are in communication with one another at the forward end of the main part. The apertures are formed in communication with the effluent passage. A rearward extension portion is coupled to a rearward end of the main part and defines an air channel in communication with the air passage and an effluent channel in communication with the effluent passage. The effluent channel within the extension does not include any apertures and is connectable to the suction source and the air channel within the extension has an open end in communication with the ambient atmosphere through an optional filter.

In another embodiment, the drainage tube includes a forward extension portion without apertures coupled to a forward end of the main part and this forward extension portion extends through the colon wall and the abdominal wall. The drainage tube also includes a rearward extension portion without apertures coupled to a rearward end of the main part and which extends out of the anus. In this embodiment, suction can be applied via a channel in either the forward or rearward extension portion with a channel in the other extension portion being open to the ambient atmosphere, through an optional filter.

In yet another embodiment, the drainage tube includes a forward extension portion coupled to a forward end of the main part and having a suction channel in flow communication with the interior lumen of the main part. The forward extension portion extends through the colon wall and the abdominal wall. The suction channel in the forward extension portion is connectable to the suction source so that in this embodiment, fecal matter is removed through the forward end of the main part. A rearward extension portion may optionally be arranged at a rearward end of the main part and defines an air inflow channel which opens to the ambient atmosphere, through an optional filter. The rearward extension portion may have a smaller cross-sectional area than the cross-sectional area of the main part and/or the interior lumen in the main part.

In still another embodiment of a drainage tube, the main part comprises both a effluent passage and an air passage such that the air passage and effluent passage are in communication with one another at the rearward end of the main part. In this case, a forward extension portion, which extends out through the colon wall and the abdominal wall, is coupled to a forward end of the main part and defines an air channel in communication with the air passage and an effluent channel in communication with the effluent passage. The effluent channel within the forward extension portion does not include any apertures and is connectable to the suction source, and the air channel within the forward extension portion has an open end in communication with the ambient atmosphere through an optional filter. Here, fecal matter is removed through the forward end of the main part.

Regardless of which construction of the drainage tube is used, it provides a suction force from either the forward end thereof or the rearward end thereof and allows an optional replenishment of air from the ambient atmosphere at the same or the opposite end of the drainage tube.

The drainage tube is provided with an appropriate length to extend substantially through the entire colon to thereby provide drainage and decompression of the entire colon. Different sized drainage tubes can be constructed for use with patients having different sized colons.

Any of the drainage tubes described above may be used in a method for draining and decompressing a colon as described below.

As such, an exemplifying method for decompressing a colon comprises the steps of inserting a drainage tube having apertures therein through the anus into the colon to extend through substantially the entire colon, fixing the drainage tube in place and applying suction from one end of the drainage tube to cause fecal matter to pass through the apertures into the drainage tube and be withdrawn from the colon. Fixing of the drainage tube in place is necessary to prevent the drainage tube from being discharged from the colon by the natural peristaltic movements of the colon or by inadvertent withdrawal.

Fixing the drainage tube in place in the colon may involve securing the drainage tube to the skin. For those embodiments which have a forward extension portion, this may mean fixing the forward extension portion to the skin by means of suture, tape or a collar. For those embodiments without a forward extension portion, this may mean attaching a filament to a forward end of the drainage tube, passing the filament through the colon wall and the abdominal wall and fixing the filament to the patient's skin. Instead of fixing the filament directly to the patient's skin, the filament can be wound onto a spool and the spool fixed onto the surface of the abdomen. The drainage tube may include an aperture formed in a tip at a front part thereof to enable the filament to be attached to the tip.

For drainage and decompression, and depending on the construction of the drainage tube, the suction can be applied continuously, intermittently or periodically. Suction can also be applied from the forward end of the drainage tube or the rearward end of the drainage tube. In the former case, when suction is applied from the forward end of the drainage tube, the drainage tube, including a main part having an interior lumen and apertures leading thereto through a wall of the drainage tube, may be connected via an extension portion having a suction channel to a suction source, i.e., the extension portion (without apertures) is passed through the colon wall and the abdominal wall and coupled to a suction device.

To enhance the performance of such drainage tubes, it is helpful to permit air to enter the tube at the point farthest from the suction supply, behind the column of effluent within the tube. This prevents the establishment of negative pressure behind the column of effluent which would impede drainage. To this end, when a drainage tube is formed so that suction is applied through the forward end of the drainage tube, a channel in a rearward extension portion of the drainage tube can be directly open to or in communication with the ambient atmosphere and the rearward extension portion can have a smaller cross-section than the main part of the drainage tube. The channel in the rearward extension portion extends out of the patient through the patient's anus to the ambient atmosphere. Otherwise, the main part of the drainage tube can be formed with two lumens, namely, an effluent passage and an air passage alongside the effluent passage and opening to the effluent passage at the rearward end of the drainage tube, but within the colon. The air passage communicates with the ambient atmosphere through an air channel in a forward extension portion of the drainage tube while the effluent passage is coupled to a suction device through a suction channel in the forward extension portion. In this manner, it becomes possible to apply suction continuously through the drainage tube.

When a drainage tube is formed so that suction is applied through the rearward end of the drainage tube, a rearward extension portion of the drainage tube, which does not include apertures communicating with an interior suction channel and is designed to extend through the patient's anus, may be directly connected to the suction source. Optionally, a channel in a forward extension portion of the drainage tube can be open to or communicate with the ambient atmosphere or the drainage tube and the forward extension portion can be formed with a smaller cross-section than the main part of the drainage tube. The forward extension portion of the drainage tube is devoid of apertures leading to the interior channel therein and extends out of the patient through the colon wall and the abdominal wall.

Otherwise, the main part of the drainage tube can be formed with two lumens, namely, an effluent passage and an air passage alongside the effluent passage and opening to the effluent passage at the forward end of the drainage tube, within the colon. The air passage communicates with the ambient atmosphere through an air channel in a rearward extension portion of the drainage tube while the effluent passage is coupled to a suction device through a suction channel in the rearward extension portion. In this manner, it becomes possible to apply suction continuously through the drainage tube Insertion of the drainage tube into a colon may entail inserting a guidewire into the colon through the anus and rectum, pushing and manipulating the guidewire forward through the colon to the cecum, threading a filament through the colon wall and into engagement with the guidewire (via a long needle or the like), withdrawing the guidewire from the colon and out of the anus to thereby draw the filament into and through the colon and out of the anus and then attaching the drainage tube to the filament. Finally, the filament is drawn back into the colon so that the attached drainage tube is drawn back through the anus into the colon until the drainage tube extends substantially entirely through the colon.

Threading the filament through the colon wall and into engagement with the guidewire may involve forming the guidewire with a through channel and passing a needle on which the filament is threaded though the channel of the guidewire. Preferably, the channel is formed in a bulbous enlargement of the guidewire to thereby provide the bulbous enlargement with flat sides. As such, the bulbous enlargement can be grasped through the bowel wall to fix the location of the flat sides so that it becomes possible to fix the location of the channel. As such, the needle with attached filament then can be easily passed through the bowel wall and channel.

Attachment of the filament to the drainage tube may involve passing the filament through a tip of the drainage tube and tying it around a wall of the drainage tube between adjacent apertures formed in the drainage tube. In the alternative, the filament may be attached to the drainage tube by passing the filament through a tip of the drainage tube and out a side hole thereof and then tying the filament to a filament button.

Fixing the drainage tube in place in the colon may entail cutting the filament which passes through the colon wall to leave a portion connected to the drainage tube, passing this portion through the abdominal wall and fixing this portion of the filament to the patient's skin. Alternatively, the filament, having been passed through the abdominal wall, can be wound onto a spool and the spool fixed onto the surface of the abdomen.

The guidewire used in the foregoing method to engage with the filament includes an elongate, resilient shaft and a bulbous enlargement arranged at a distal end of the shaft. The bulbous enlargement has a smooth, arcuate outer surface to prevent damage to the walls of the colon during movement of the guidewire through the colon and includes an engagement structure which enables engagement of the filament thereto. Specifically, the engagement structure may take the form of a channel extending through the bulbous enlargement. This provides the bulbous enlargement with opposed flat sides which can be easily felt to thereby enable the location of the channel to be determined by the surgeon by touch alone. The channel may have an axis perpendicular to an axis of the shaft.

BRIEF DESCRIPTION OF THE DRAWINGS

The invention, together with further objects and advantages thereof, may best be understood by reference to the following description taken in conjunction with the accompanying drawings wherein like reference numerals identify like elements.

FIG. 2 is a side view of the first embodiment of a guidewire in accordance with the invention.

FIG. 3 is a front view of the guidewire shown in FIG. 2.

DETAILED DESCRIPTION OF THE INVENTION

Figure 1:
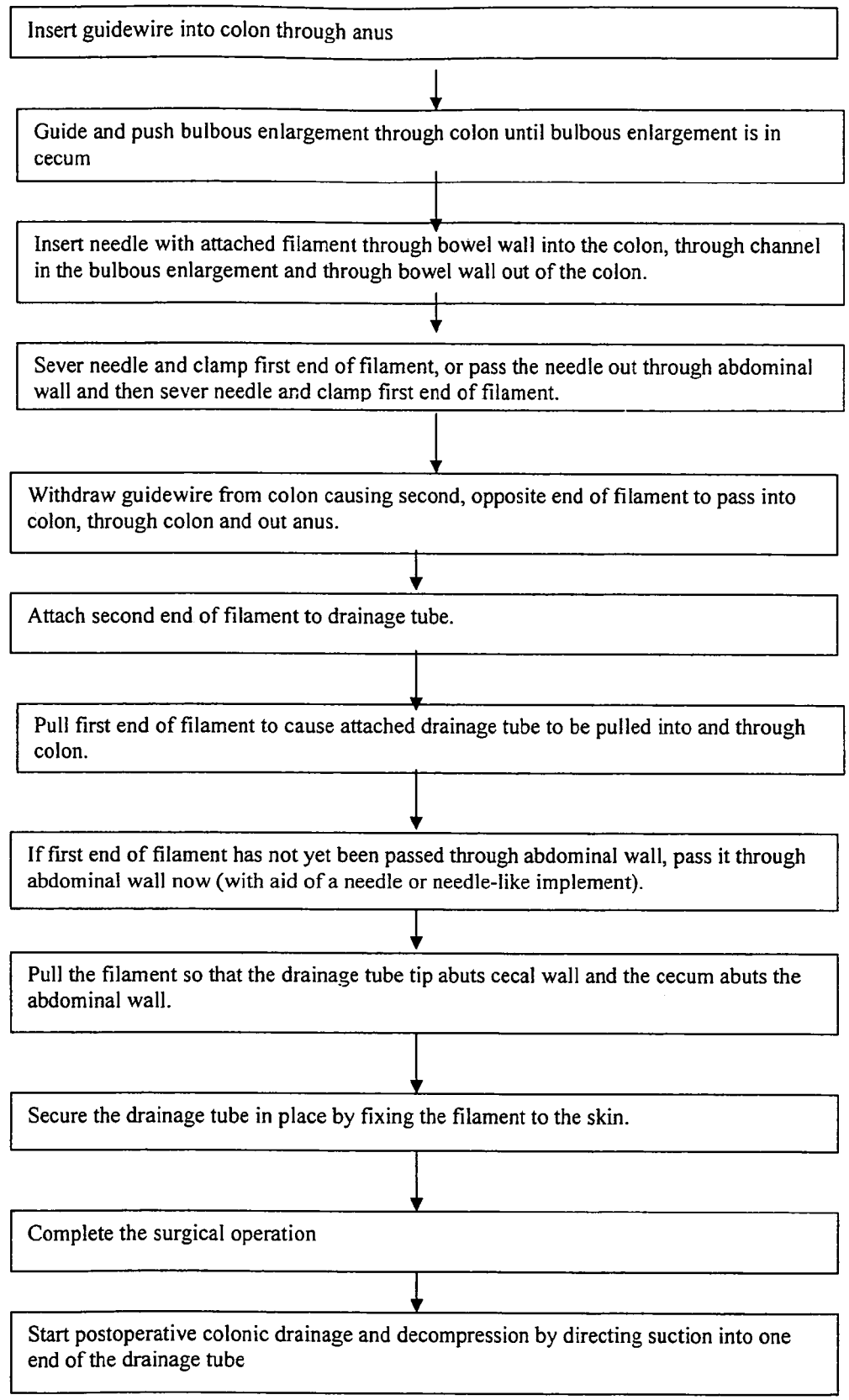
FIG. 1 is a chart of the steps in a method for inserting a drainage tube into a colon and steps in a method for decompressing and draining the colon in accordance with the invention.

Referring to the accompanying drawings wherein like reference numerals refer to the same or similar elements, the present invention relates generally to a drainage tube for insertion into the colon, a method for draining the colon using such a drainage tube, a method for inserting such a drainage tube into the colon such that it is extends substantially through the entire colon, and a guidewire for aiding insertion of a drainage tube into the colon. Once the drainage tube is positioned in the colon, suction can be applied to drain and decompress the colon, removing fecal matter therefrom. By continually removing fecal matter from the colon via the drainage tube, a newly created anastomosis in the colon can be protected from distension and fecal soilage, and, should there be a defect in the anastomosis, leakage of gas or fecal matter through that defect into the peritoneal cavity can be minimized.

One method for inserting a drainage tube into the colon in accordance with the invention is outlined in FIG. 1 in a case where the drainage tube is being inserted after a section of colon has been removed and an anastomosis formed to restore the continuity of the colon. However, the method has various optional steps and variations, as will be discussed below, and is not limited to the steps shown in FIG. 1. Moreover, the steps are not required to be performed in the order shown in FIG. 1 and various changes in the order are possible, some of which are discussed below.

The first step in the method (step 10) is to insert a guidewire 50 into the colon through the anus and rectum. The guidewire 50 is then pushed and manipulated forward through the colon to the most proximal portion of the colon, i.e., the cecum (step 12). The abdominal cavity is open for surgery and the surgeon facilitates passage of the guidewire 50 by manipulating the bowel and the head of the guidewire within the bowel.

Guidewire 50 has a unique construction in accordance with the invention to enable it to be easily inserted into the anus and manually pushed, guided and manipulated through the colon. As shown in FIG. 2, the guidewire 50 includes an elongated, resilient wire or shaft 52 and a bulbous enlargement 54 attached at a terminal end of the shaft 52 and having a forward-facing smooth, arcuate surface 56 to enable the bulbous enlargement 54 to slide along the walls of the colon as it is pushed forwardly through the colon (during insertion through the colon as discussed above). Moreover, the bulbous enlargement 54 has a rearward-facing smooth, arcuate surface 58 to enable the bulbous enlargement 54 to slide along the walls of the colon when the guidewire 50 is withdrawn from the colon (as discussed below). The smoothness of the forward-facing surface 56 and rearward-facing surface 58 inhibits injury or perforation of the wall of the colon when the bulbous enlargement 54 makes contact therewith.

As shown in FIG. 3, a channel 60 is formed in the bulbous enlargement 54 extending between opposed sides of the bulbous enlargement 54 to provide the bulbous enlargement with opposed flat sides 60a, 60b. Since the flat sides 60a, 60b of the bulbous enlargement 54 indicate the presence of the openings of the channel 60, it is readily possible to locate the openings of the channel 60 by feeling for the flat sides 60a, 60b of the bulbous enlargement 54 through the bowel wall.

The channel 60 is preferably formed so that the flat sides 60a, 60b are laterally facing in order to maintain the presence of both the forward-facing arcuate surface 56 and the rearward-facing arcuate surface 58. The channel 60 is designed to enable a needle threaded with filament to be passed therethrough, the purpose of which is discussed more fully below.

Channel 60 may be an axial channel extending through an axis of the bulbous enlargement 54 which is perpendicular to an axis through the shaft 52. The channel 60 may have a circular cross-section or any other cross-section. Other constructions of channels can be formed, provided that at least an entrance to the channel is discernible, for the reason discussed below. Thus, instead of forming the channel 60 to provide the bulbous enlargement 54 with the two discernible flat sides 60a, 60b, it is conceivable to provide only a single discernible flat side forming an entrance to the channel 60. Other constructions which enable the opening of the channel to be discernible by touch are also envisioned within the scope and spirit of the invention.

The bulbous enlargement 54 is, like the shaft 52, made of a material compatible for insertion into and contact with internal body cavities, such materials being known to those skilled in the art. Also, the bulbous enlargement 54 should be sufficiently rigid to enable it to be easily passed through the colon, although the shaft 52 is flexible. Bulbous enlargement 54 may be formed from metal or plastic. Shaft 52 may be formed from metal or plastic (e.g., TEFLON™) optionally encased in a sheath. If formed of metal, the shaft 52 may be formed from a metal such as Nitinol™ which has superior memory properties. The bulbous enlargement 54 may have a diameter of about 0.25 inches to about 0.75 inches. A more specific range would be from about 0.5 inches to about 0.75 inches.

Figure 4:
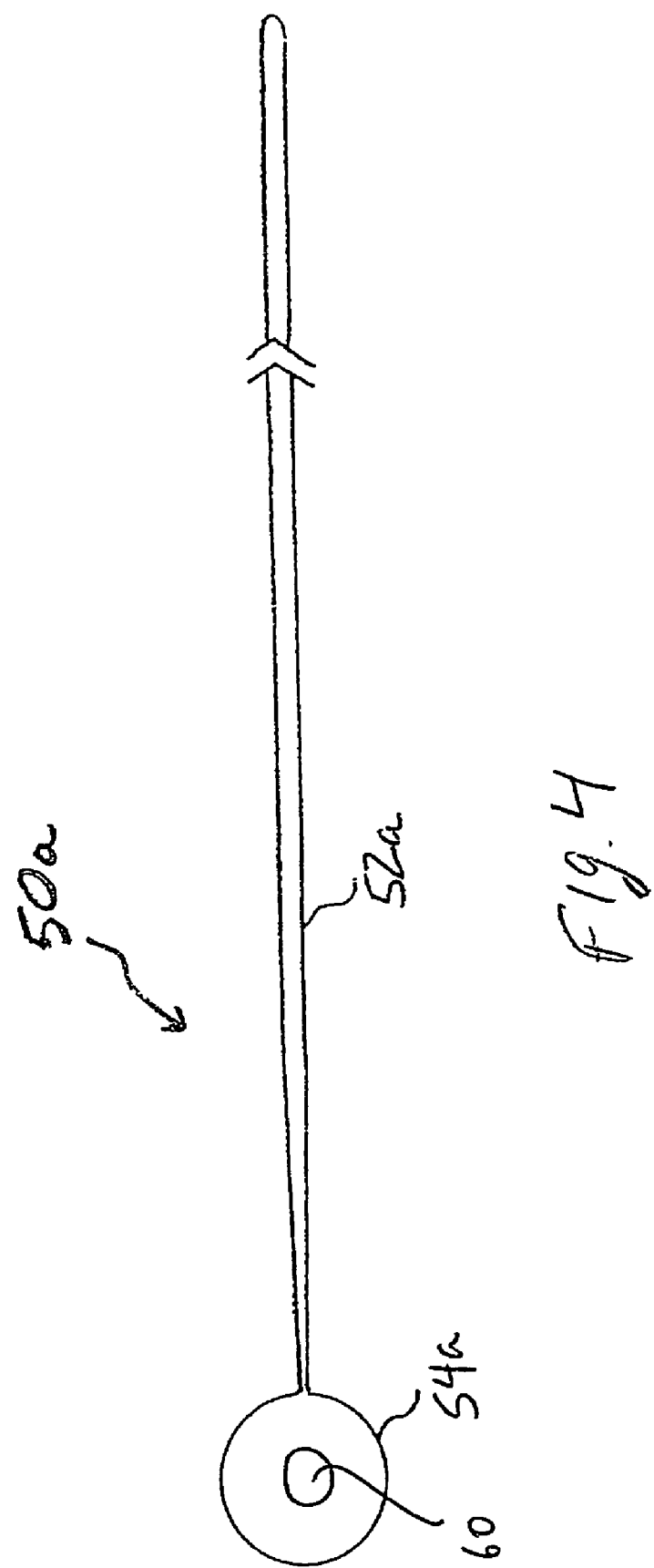
FIG. 4 is a side view of a second embodiment of a guidewire in accordance with the invention.

FIG. 4 shows a second embodiment of a guidewire, designated 50a, having a shaft 52a having a substantially circular cross-section and which is tapered so that its diameter in proximity to the bulbous enlargement 54 is smaller than its diameter farther from the bulbous enlargement 54. This gives the guidewire 50a more flexibility near the bulbous enlargement 54, facilitating manipulation of the bulbous enlargement 54 and advancement through the bowel. Instead of a circular cross-section, the shaft 52a may have other cross-sectional shapes.

Figure 5:
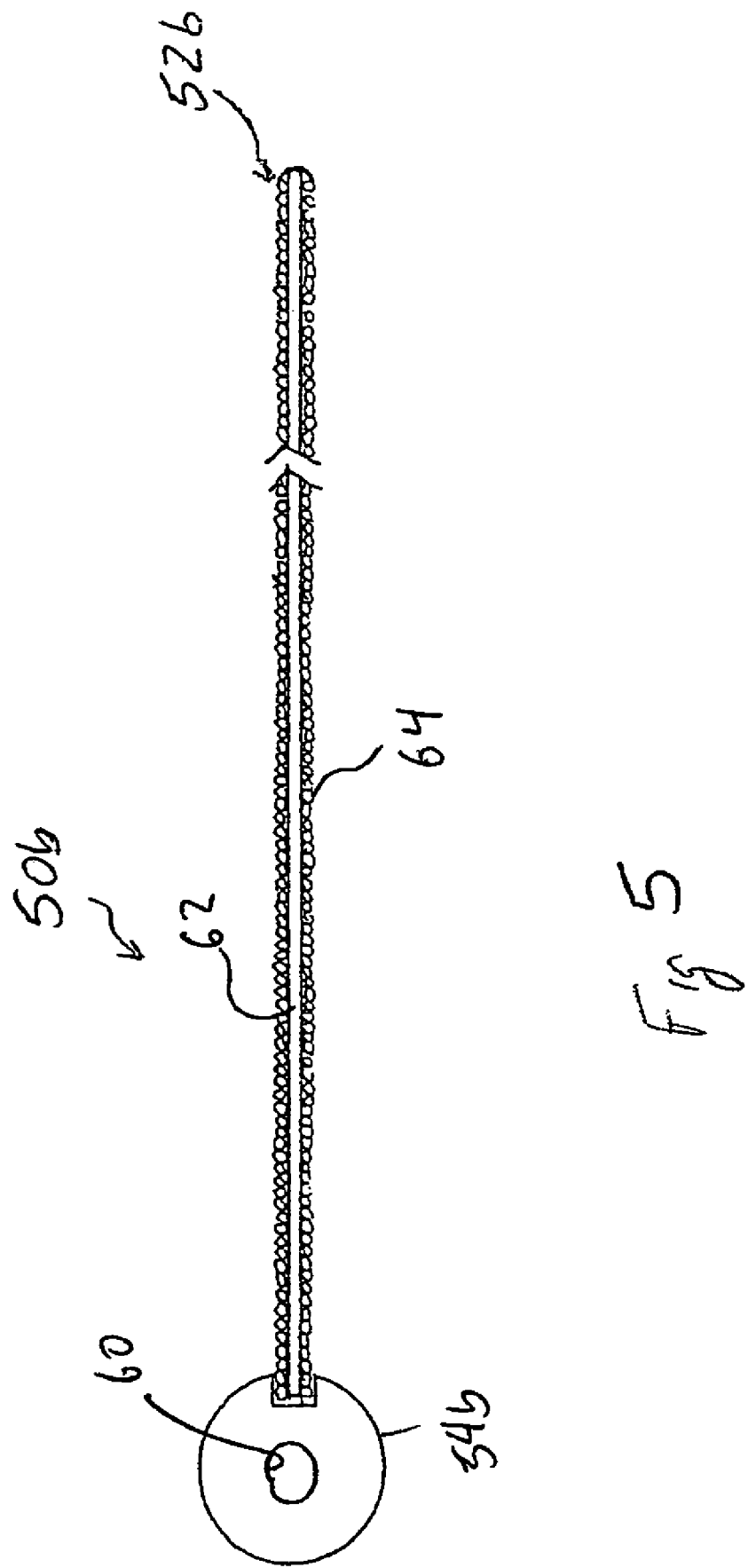
FIG. 5 is a side view of a third embodiment of a guidewire in accordance with the invention.

FIG. 5 shows a third embodiment of a guidewire 50b having a shaft 52b which is constructed of a straight or tapering central metal core wire 62 surrounded by a wire coil 64. This configuration increases the diameter of the shaft 52b while maintaining the flexibility of the shaft 52b. The larger diameter of the shaft 52b allows for easier and safer handling of the guidewire 50b and makes it less likely to damage the wall of the bowel.

It is also conceivable to make the shaft 52 of the guidewire 50 of constant diameter throughout, but with the portion thereof attached to the bulbous enlargement 54 more flexible than the remainder of the shaft 52. For example, the flexibility of a segment of metal or plastic can be increased without altering its diameter. Another option is to form the shaft from a tapering metal core surrounded by a constant diameter coil.

Figure 6:
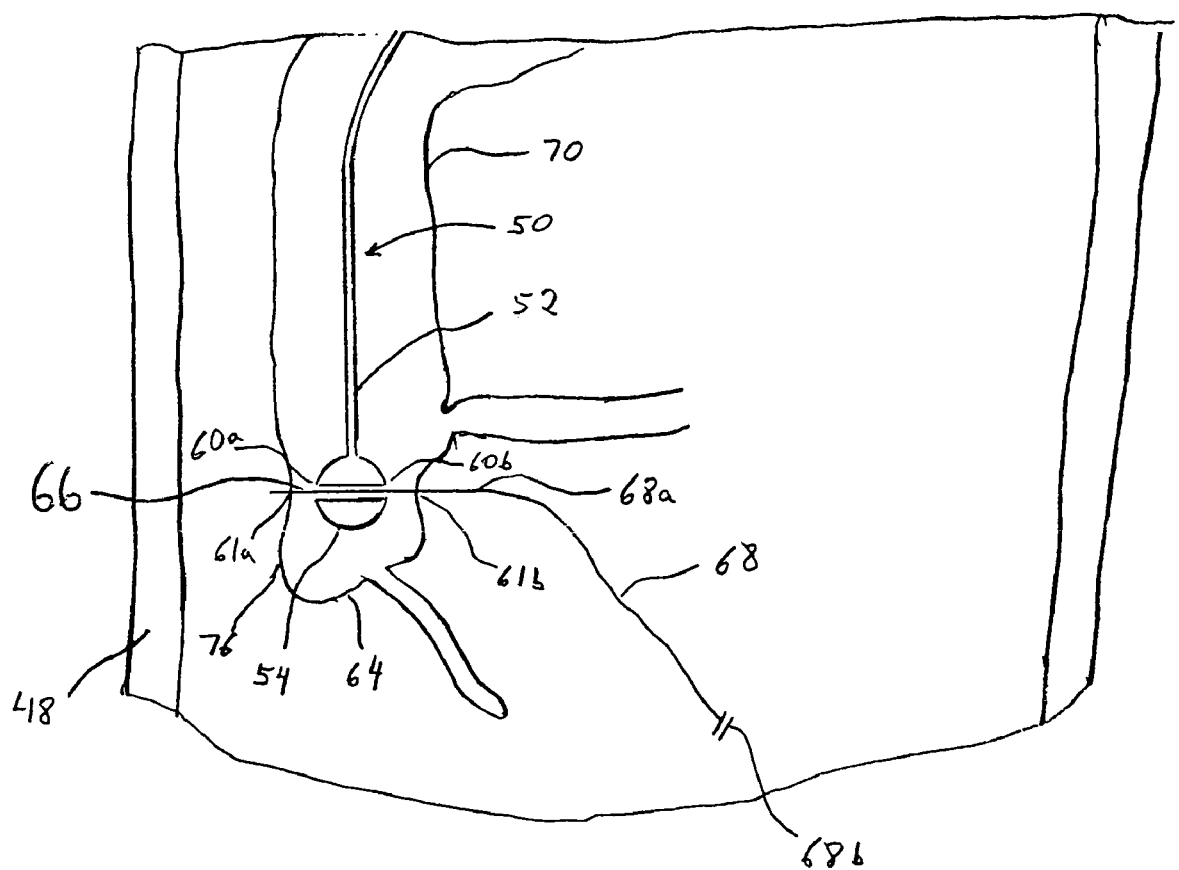
FIG. 6 is a schematic showing the manner in which a needle is passed through a channel in a part of the guidewire to couple a filament to the guidewire.

Referring back to FIG. 1, after the guidewire 50 is situated in the colon with the bulbous enlargement 54 at the most proximal portion thereof, usually the cecum, (as shown in FIG. 6), the colon 70, including the most proximal part of the colon known as the cecum 64, is then manipulated until the bulbous enlargement 54 can be grasped and oriented to locate the flat sides 60a and 60b of the bulbous enlargement 54, and thus the location of the channel 60. A needle 66 with attached filament 68 is then pushed through the wall 76 of the cecum 64 and into the entrance to the channel 60, through the channel 60 and out from the cecum 64 through the cecal wall 76 (step 14) (see FIG. 6). For the needle 66, a straight needle could be used and swedged to the forward end 68a of a long filament 68. The needle 66 may then be held while the next steps are completed, or cut off and the forward end 68a of the filament 68 (that end which had been attached to the needle 66) clamped, or passed through the abdominal wall 48, inside to outside, and then cut off and the forward end 68a of the filament 68 clamped (step 16). In the alternative, a long needle which has a lumen, such as a spinal needle, could be passed through the cecum 64 and the channel in the bulbous head of the guidewire and the forward end 68a of the filament 68 then passed retrograde through the needle, the needle then immediately removed, and the forward end 68a of the filament 66 clamped.

Figure 7:
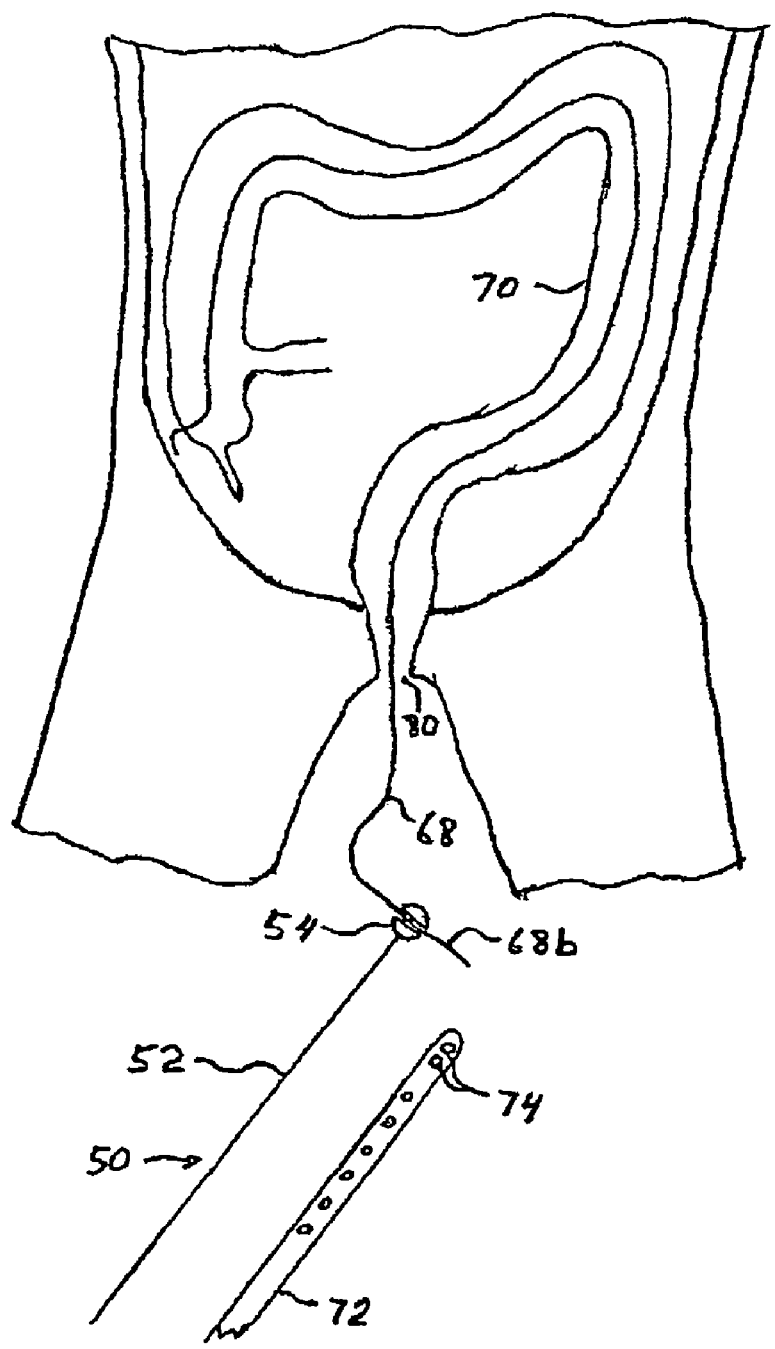
FIG. 7 is a schematic showing the manner in which the guidewire is withdrawn from the colon with one end of the filament which is to be attached to a drainage tube.

The guidewire 50 is then withdrawn from the colon 70 and out from the anus by pulling a rearward end of the guidewire 50 (step 18). Since the forward end 68a of the filament 68 is clamped or held after exiting the cecal wall 76 at point 61a, as the guidewire 50 is withdrawn, the guidewire 50 pulls more filament 68 into the colon 70 through the cecal wall 76 at point 61b, until the end 68b of the filament 68 is drawn into the colon 70, and distally (towards the anus 80) through the colon 70 until the end 68b of the filament 68 comes out of the anus 80. The length of the filament 68 should thus be longer than the length of the colon 70 so that it is extended out from the patient's anus as the guidewire 50 is withdrawn (see FIG. 7). Once a portion of the filament 68 has exited the anus 80 and is manually graspable, the guidewire 50 can be slid off of the filament 68.

Thus, a single strand of filament 68 is drawn distally through the colon 70 by the guidewire 50. One end 68b of this strand of filament 68 is available for attachment to the drainage tube 72, described below, and the other end 68a of the filament 68 is situated outside of the cecum 64 and can be used to pull the drainage tube 72 proximally through the colon 70.

The construction of the bulbous enlargement 54 of the guidewire 50 with the channel 60 enables a single strand of filament 68 to be passed through the colon 70 (as opposed to a double strand). That is, the strand of filament 68 can slide through the channel 60 as the guidewire 50 is being pulled distally through the colon 70 and enables the bulbous enlargement 54 to be slid off of the filament 68 once the bulbous enlargement 54 is outside of the anus 80. By contrast, if the filament 68 were to be clamped to the bulbous enlargement 54, a double strand of filament 68 would be pulled into and through the colon 70.

The primary purpose of the guidewire 50 is therefore to lead the filament 68 in a distal direction from the most proximal portion of the colon 70 through the colon 70 and out of the patient through the anus 80. As such, the guidewire 50 includes structure to engage with the filament 68, for example, the channel 60 formed in the bulbous enlargement 54 through which the filament 68 can be threaded. The construction of the guidewire 50 may be modified from that described above but at a minimum, should include or incorporate a structure which enables a filament to be engaged therewith and causes the filament to be moved along with movement thereof. For example, instead of a channel extending through the bulbous enlargement, it is conceivable that an annular ring might be formed on the bulbous enlargement through which the filament can be passed. Also, it is conceivable that the bulbous enlargement might be eliminated, and replaced with a ring or hook, although this would detract from the ability of the guidewire to pass smoothly along the walls of the bowel and prevent injury of the bowel walls.

It is envisioned that the guidewire 50 and filament 68 would be most usually passed through the colon 70 after the diseased segment of the colon 70 was removed and the continuity of the colon re-established by anastomosis. However, it is possible that the surgeon passes an implement through the colon 70 prior to colonic resection. This might be done, for example, as part of a process to irrigate and cleanse the colon 70 before it is operated upon. Then, already having an implement running through the entire colon 70, the surgeon may want to attach a filament 68 to the forward end of the implement (e.g., irrigating tube or irrigating tube guidewire) and pull the filament 68 through the bowel when he withdraws the implement. At this stage, the surgeon would resect the colon 70, severing the filament 68 and removing a section of it with the resected bowel. The two severed ends of the remaining filament segments would then be rejoined when the anastomosis is performed. When a transanal circular stapling instrument is used to form the anastomosis, the rearward end of the segment of filament in the proximal colon can be attached to the anvil of the stapler and pulled through the anus when the stapler is removed. Regardless of whether the filament is passed through the colon before or after resection of the diseased colon segment, the filament 68 should extend from its point of introduction proximate the cecum 64 entirely through the colon 70 and out of the anus 80.

After the guidewire 50 is separated from the filament 68, the next step is to attach the drainage tube 72 to the end 68b of the filament 68 (step 20). As the filament 68 is exterior of the patient, this attachment will also occur outside the patient (see FIG. 7).

Figure 8A:
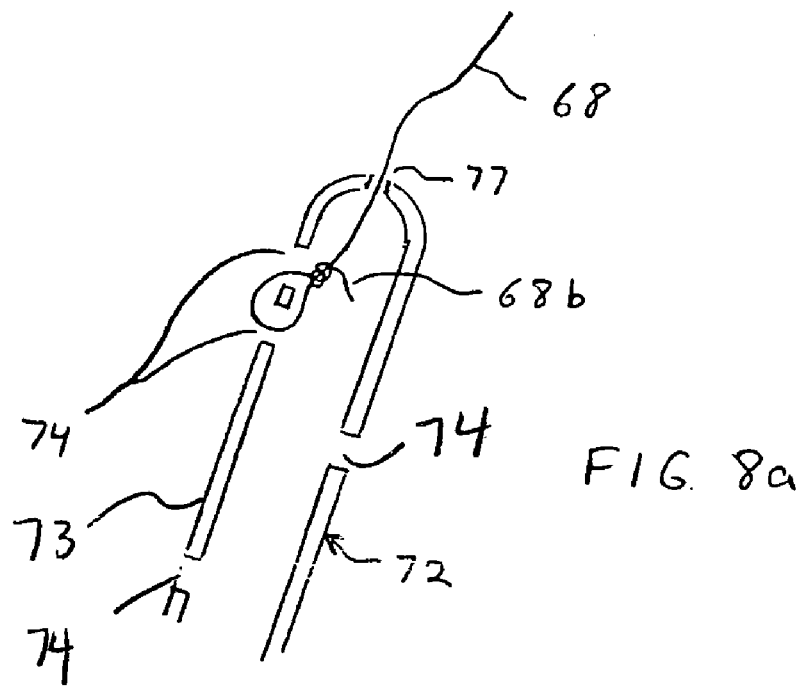
FIG. 8A is a schematic showing one manner in which the filament is attached to the drainage tube.
Figure 8B:
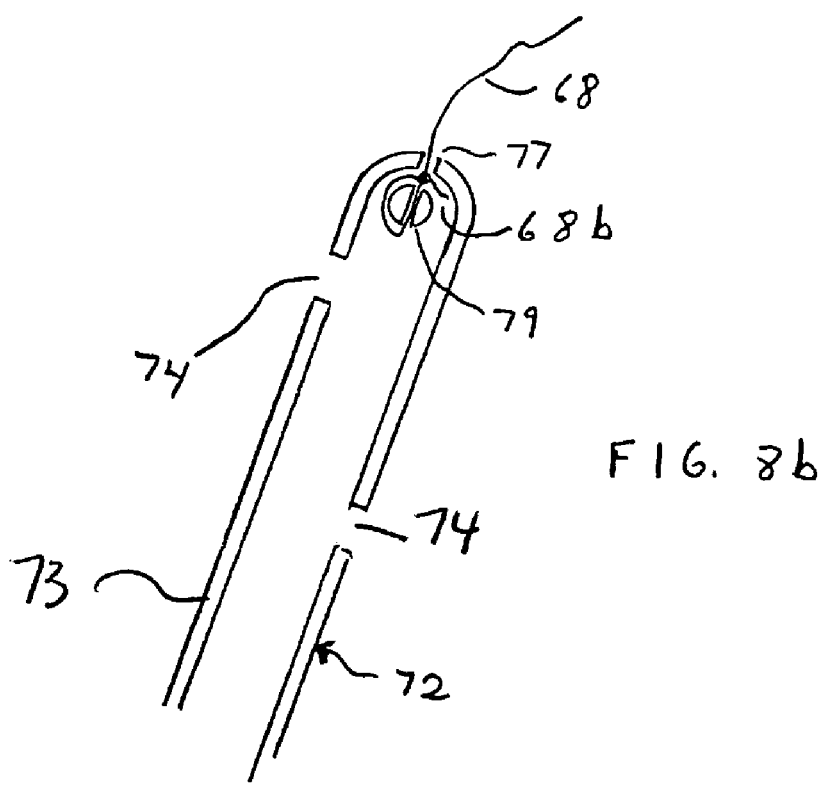
FIG. 8B is a schematic showing another manner in which the filament is attached to the drainage tube.

Attachment of the filament 68 to the drainage tube 72 may involve tying the filament 68 to the drainage tube 72, e.g., passing the filament 68 through a small aperture 77 in the tip of the drainage tube 72 and tying it around a wall of the drainage tube 72 between two adjacent apertures 74 of a main body part of the drainage tube 72 (see FIG. 8A). Other attachment techniques may also be used, such as passing the filament 68 through a small aperture 77 in the tip of the drainage tube 72 and out a side hole thereof and then tying the filament 68 to a filament button 79. The end 68b of the filament 68 and attached filament button 79 are then withdrawn into the tip of the drainage tube 72 until the filament button 79 abuts against the inner surface of the tip of the drainage tube 72 (see FIG. 8B). The filament button 79 is too large to pass out of the tip through the small aperture 77 in the tip so that the filament 68 is thereby secured to the drainage tube 72. In this case, if the filament button 79 is made of metal, it would provide a radiopaque marker for the position of the tip of the drainage tube 72.

It is also possible to mark the tip of the drainage tube 72 with a radiopaque line, or place a radiopaque line along the entire length of the drainage tube 72, or form the entire drainage tube 72 using a radiopaque material to enable the position of the drainage tube 72 to be determined during X-ray examination.

A Reverdin needle, or other suture passing implement, can assist in passing the filament 68 through the tip of the drainage tube 72, either through a small aperture 77 or directly through the plastic wall of the tip, and in tying it to the wall of the drainage tube 72. Regardless of which attachment technique is used to connect the filament 68 to the drainage tube 72, the filament 68 should not detach from the drainage tube 72 when tension is placed on the filament 68.

Once the drainage tube 72 is secured to the end 68b of the filament 68, the filament 68 is then pulled back (e.g., by pulling the end 68a) and the attached drain tube 72 is drawn through the anus 80 into the colon 70 and through the colon 70 until its tip is situated in the cecum 64 (step 22). The filament 68 is cut leaving only a portion connected to the drainage tube 72

Figure 10:
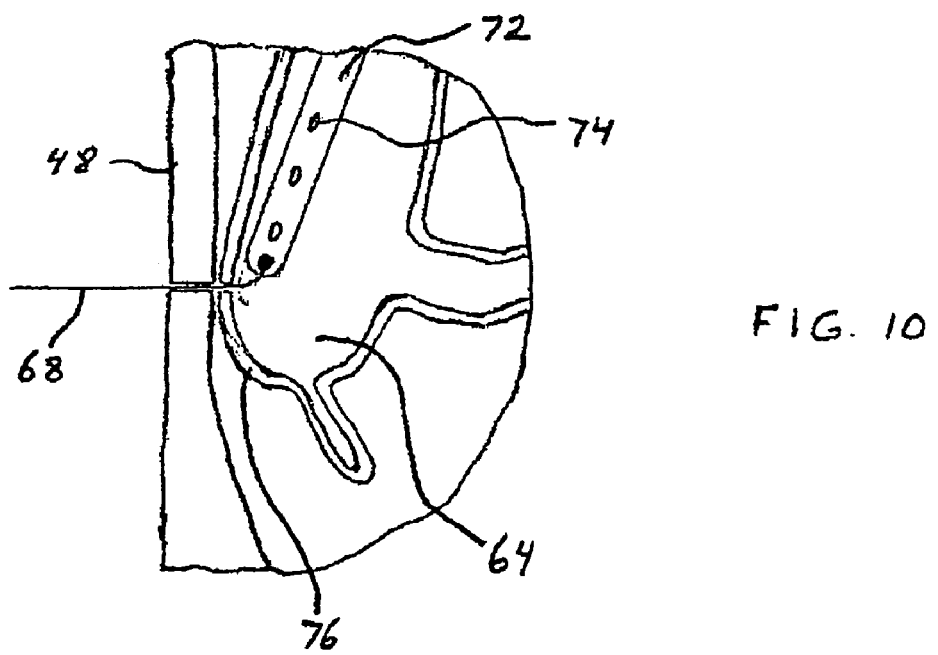
FIG. 10 is an enlarged view of the portion designated 10 in FIG. 9.

If the end 68a of the filament 68 has not yet been passed through the abdominal wall 48, then it is now passed through the abdominal wall, for example, with the aid of a needle or needle-like implement (step 24). The filament 68 is now pulled so that the tip of the drainage tube 72 abuts the wall 76 of the cecum 64 and the cecum 64 abuts the abdominal wall 48 (step 26-FIG. 10).

The drainage tube 72 is now fixed in place in the colon 70 (step 28). Fixing the drainage tube 72 in place prevents peristalsis from ejecting the drainage tube 72 from the colon 70. Such fixing of the drainage tube 72 may entail passing the filament 68 through the abdominal wall and stitching it, for example, with the aid of a needle, to the patient's skin. In the alternative, a relatively large length of the filament 68 can be left and wound onto a spool which is then held on the abdominal surface. In this case, when the drainage tube 72 is subsequently removed from the colon 70, the filament 68 will unwind from the spool and pass into and through the colon 70. The thin filament can be re-secured so that it stays situated through the colon 70 so that it will be available to facilitate subsequent emergency reintubation, if necessary. The filament 68 can then be removed when recovery from the surgery is assured.

After the tip of the drainage tube 72 is fixed, the surgical operation is completed (step 30) and the drainage tube 72 is prepared for use in draining and decompressing the colon 70. Postoperative colonic drainage and decompression are started by attaching the rearward end of the drainage tube 72 to a suction device 78 (step 32).

Figure 9:
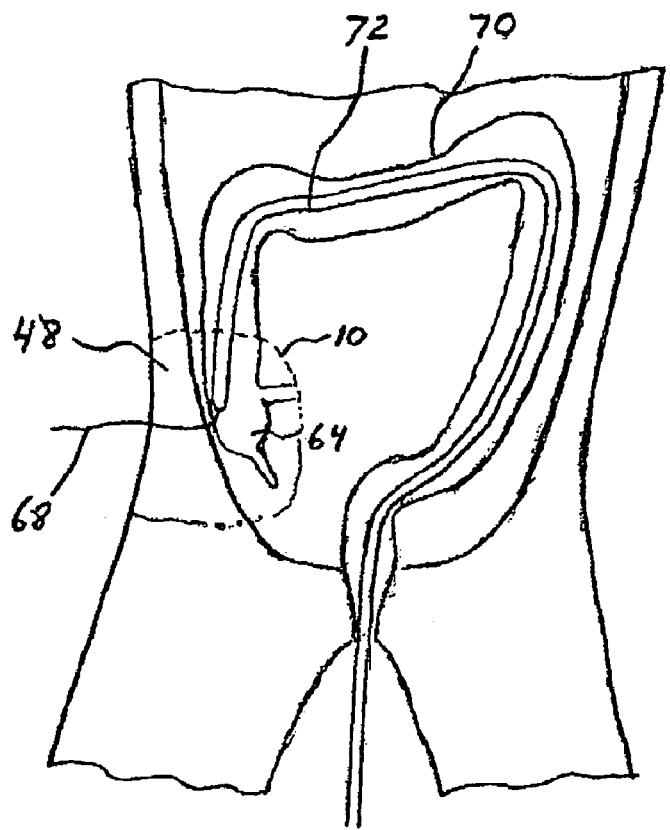
FIG. 9 is a schematic showing the state at which the drainage tube extends to the most proximal portion of the colon.

The drainage tube 72 includes a main or intracolonic part 73 which is that portion of the drainage tube 72 which will be situated in the patient's colon 70. To this end, the main part 73 includes a lumen and apertures 74 extending between the inner and outer walls defining the main part 73 and communicating with the lumen. The suction device 78 applies suction through the lumen of the drainage tube 72 which is effective to draw fecal matter from the colon 70 and into the lumen of the drainage tube 72 through the apertures 74 formed in the drainage tube 72 (see FIG. 9). The presence of the drainage tube 72, extending from the most proximal portion of the colon 70 through the entire colon, draws fecal matter from the entire colon 70, prevents distention of the colon 70, and if there is a defect in the anastomosis, minimizes the escape of gas, and feces into the peritoneal cavity.

Figure 11:
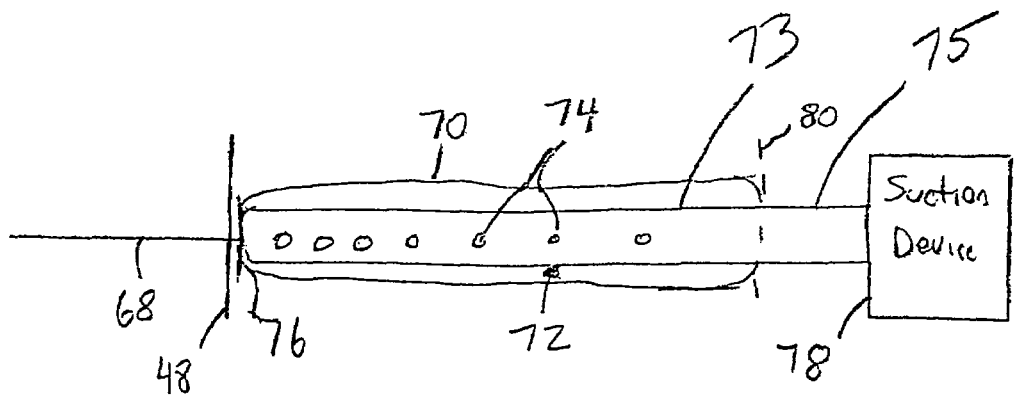
FIG. 11 is a schematic showing one embodiment of a first embodiment of a drainage tube in accordance with the invention when used for colonic drainage and decompression.

FIG. 11 diagrammatically shows the position of the drainage tube 72 when operatively situated in the colon 70 with its forward end connected to the filament 68 which fixes the forward end in position and with a rearward extension portion 75 extending out of the anus 80. The rearward extension portion 75 is arranged rearward of the main part 73 and includes a channel which communicates with the lumen in the main part 73. The filament 68 is shown extending outward from an indicator of the cecal wall 76 to outside of the abdominal wall 48. The drainage tube 72 is shown extending through the entire colon 70 and extending out of the anus 80.

The apertures 74 may be equally spaced along the length of the main part 73 of the drainage tube 72 or may be variably spaced with more apertures 74 closer to the forward end of the main part 73 of the drainage tube 72. The size of the apertures 74 may be the same throughout the entire main part 73 of the drainage tube 72 or varied to provide larger apertures closer to the forward end of the main part 73 of the drainage tube 72. Generally, more aperture area is desired at the forward end of the main part 73 of the drainage tube 72 since the fecal matter enters the colon in the vicinity of the forward end.

During use of the drainage tube 72, the colon 70 is drained and decompressed and maintained in a decompressed state by the application of continuous or intermittent suction applied by the suction device 78 connected to the drainage tube 72. The suction force runs through the entire drainage tube 72 which extends through substantially the entire colon 70 so that the suction force is applied through the entire colon 70. By diverting the fecal matter away from an anastomosis, and keeping the colon decompressed, postoperative complications and anastomotic leakage and its septic sequelae are minimized. Intra-abdominal pressure is minimized resulting in decreased wound dehiscence and evisceration rates and improved pulmonary function. Early feeding of the patient is more successful as it is not limited by colonic distension. Such enhanced early feeding and improved respiration hasten the patient's recovery.

Appropriate use of the drainage tube 72 will reduce the complications of colectomy, and permit safe anastomosis even in circumstances where primary anastomosis was heretofore considered too dangerous to attempt. The use of both diverting proximal ostomies and temporary end colostomies will therefore be diminished.

Additional advantages of the use of the drainage tube 72 in accordance with the invention include the fact that total colonic decompression in the immediate postoperative period prevents colonic distention. Diminished intracecal pressure promotes small bowel emptying. Nausea, vomiting, and the discomfort associated with distended bowel are minimized. The decreased colonic volume reduces abdominal compartment pressure, improves visceral circulation, renal perfusion and reduces strain on the abdominal wound. Further, the decreased colonic wall tension improves colonic blood flow and perfusion of the healing anastomosis. Continuous aspiration of small bowel effluent and negative intracolonic pressure prevents anastomotic leakage.

Furthermore, the invention provides a novel indwelling colonic tube which facilitates postoperative testing for anastomotic leak in high risk cases or when leak is suspected. Anastomotic defects could be more easily detected and treated before a catastrophic leak occurs. An anastomotic defect might be treated by prolonged colonic intubation and aspiration, avoiding the need for surgical intervention.

The foregoing advantages might influence surgeons to favor resection and anastomosis without ostomy in emergency and high risk elective operations, such as coloanal and ileal pouch-anal anastomoses, or operations for acute diverticulitis.

Another significant improvement is that since both small bowel and gastric ileus resolve by 48 hours, early postoperative feeding would succeed more consistently when colonic content is effectively aspirated. However, for the tube to effectively aspirate the liquid effluent entering the proximal colon, the fiber content of the effluent must be low and therefore the diet should be fiber-free. Intravenous lines can be removed earlier and the patient switched sooner to oral medication. Delivery of agents such as fatty acids and growth factor directly to the anastomotic region via the colonic tube might speed the healing process. With skilled home nursing care earlier hospital discharge may be possible.

In the above-described embodiment, suction is applied by the suction device 78 from a rearward end of the drainage tube 72 and thus the fecal matter entrained by the suction force moves distally through the colon 70. Since the proximal end of the colon 70 does not allow air inflow, except for the small amount delivered by the small bowel, injury to the mucosal lining of the bowel could result from continuous suction force at the tubes apertures. In order to prevent injury to the bowel which might occur if sustained suction were applied, the suction force provided by the suction device 78 is preferably applied only intermittently, i.e., applied for a few moments, then turned off, then reapplied, turned off and so on.

Figure 12:
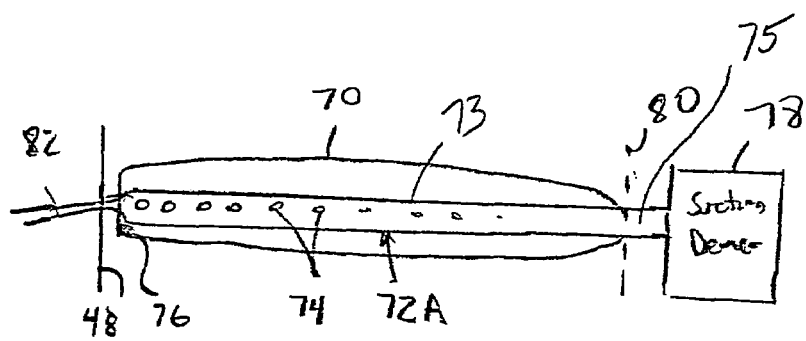
FIG. 12 is a schematic showing one embodiment of a second embodiment of drainage tube in accordance with the invention when used for colonic drainage and decompression.

However, as shown in FIG. 12, it is also possible to use a drainage tube 72A which includes a forward extension portion 82 having an air inflow channel at the forward end of the drainage tube 72A and which extends outside of the patient's body through the colonic wall 76 and abdominal wall 48. Forward extension portion 82 has a smaller cross-sectional area than the main part 73 of the drainage tube 72A in which the apertures 74 are formed. Forward extension portion 82 is provided with an open forward end communicating with the ambient atmosphere and this allows suction to be applied continuously by the suction device 78 to the rearward extension portion 75, without injury to the bowel wall. An optional filter may be used to filter the flow of air into the forward extension portion 82.

An air flow is created by the suction device 78 from the open forward end of the tube, through the air inflow channel in forward extension portion 82, through the lumen in the main part 73 of the drainage tube 72A and through the channel in the rearward extension portion 75. Fecal matter is drawn through the apertures 74 in the main part 73 of the drainage tube 72A and sucked out of the colon 70 to a waste collection device associated with the suction device 78 (not shown). The air inflow actually improves the performance of the drainage tube 72A by preventing the formation of a vacuum behind the fecal effluent, which would resist emptying of the drainage tube 72A.

The forward extension portion 82 may be secured, e.g., to the patient's skin, in order to fix the drainage tube 72A in position. Care must be exercised to avoid occluding the air inflow channel in the forward extension portion 82 when fixing the forward extension portion 82 to the patient. When the forward extension portion 82 is present, the end 68b of the filament 68 may be attached to the forward extension portion 82 in order to draw the drainage tube 72A into and through the colon 70. Pulling of the end 68a of the filament 68 is continued until the forward extension portion 82 extends through the cecal wall 76 and the abdominal wall 48 so that the forward end of the main part 73 abuts the cecal wall 76, and the filament 68 is then removed.

Figure 13:
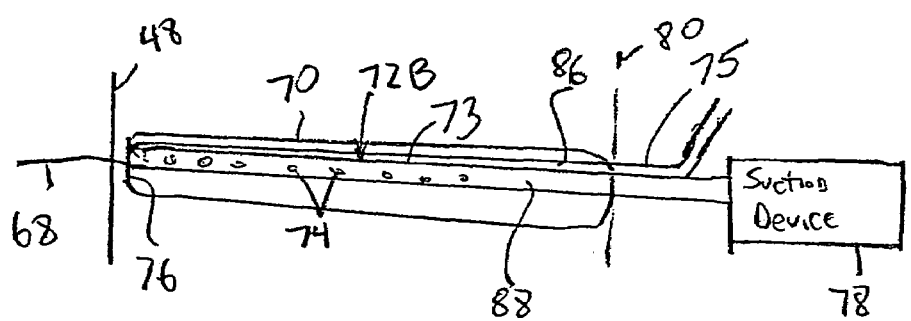
FIG. 13 is a schematic showing one embodiment of a third embodiment of a drainage tube in accordance with the invention when used for colonic drainage and decompression.
Figure 14:
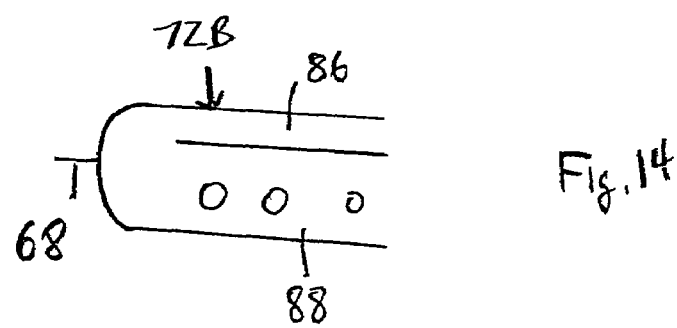
FIG. 14 is an enlarged view of the forward end of the drainage tube shown in FIG. 13.

Another manner to introduce air into the forward end of the drainage tube 72 is to construct a drainage tube 72B with a main part 73 having two lumens, an effluent passage 88 and an air passage 86 alongside an effluent passage 88 (see FIGS. 13 and 14). The apertures 74 are formed in connection with the effluent passage 88. The forward end of the air passage 86 opens at the forward end of the main part 73 of the drainage tube 72B into the effluent passage 88 and the rearward end of the air passage 86 is in continuity with an air channel in a rearward extension portion 75 of the drainage tube 72B which is open and communicates with the ambient atmosphere. The rearward extension portion 75 also includes an effluent channel which communicates with the effluent passage 88 in the main part 73 and leads to the suction device 78. By enabling air to be replenished at the forward end of the drainage tube 72B, one can expedite the passage of fecal matter through the drainage tube 72B since the formation of a vacuum behind the fecal matter is prevented. When suction is applied, air is drawn from the ambient atmosphere, through the air channel in the rearward extension portion 75, through the air passage 86 and then through the effluent passage 88 to a waste collection device (not shown) associated with the suction device 78.

The forward end of the drainage tube 72B is fixed in position by the filament 68 in the same manner as described in connection with the embodiment shown in FIG. 11.

In the embodiments of the drainage tube shown in FIGS. 11-14, suction is applied from the rearward end of the drainage tube 72, 72A, 72B so that the fecal matter flows within the tube in a distal direction through the colon 70 and out of the colon 70 through the anus 80. An alternative is to apply suction from the forward end of the drainage tube so that fecal matter flows in a proximal direction through the colon and out of the colon through the abdominal wall.

Figure 15:
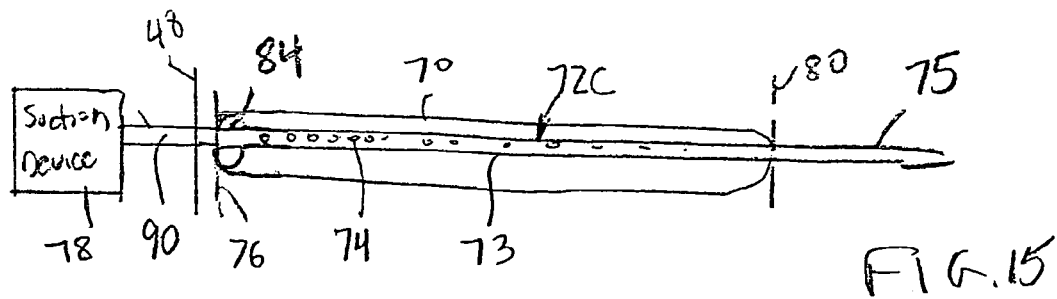
FIG. 15 is a schematic showing one embodiment of a fourth embodiment of a drainage tube in accordance with the invention when used for colonic drainage and decompression.

A first embodiment applying this alternative is shown diagrammatically in FIG. 15 wherein the drainage tube 72C has a main part 73 having a substantially uniform cross-section and a forward extension portion 90 of the drainage tube 72C passes through the cecal wall 76 and the abdominal wall 48. The forward extension portion 90 includes a channel communicating with the interior lumen in the main part 73. Apertures 74 are formed only in that portion of the drainage tube 72C that will be situated in the colon 70, i.e., the main part 73, and not in the forward extension portion 90 situated between the cecal wall 76 and the suction device 78.

The forward extension portion 90 of the drainage tube 72C can be coupled to a suction device 78. A rearward extension portion 75 of the drainage tube 72C includes a channel communicating with the interior lumen in the main part 73 and which is then left open to the ambient atmosphere. As such, the suction device 78 creates an air flow passing in a forward direction through the drainage tube 72C, i.e., from the ambient atmosphere, into the drainage tube 72C and through the drainage tube 72C to the suction device 78. Preferably continuous suction is utilized. A waste collection device (not shown) is associated with the suction device 78 to remove fecal matter drawn by the suction force into the drainage tube 72C.

For this embodiment, it also possible to reverse the position of the suction device 78 and the open end of the drainage tube 72C communicating with the ambient atmosphere so that an air flow in a rearward direction through the drainage tube 72C is created (as for drainage tubes 72, 72A and 72B described above).

The forward end of the drainage tube 72C is fixed to the skin with suture or tape or secured with a collar.

In view of the presence of the forward extension portion 90 (in the embodiment above as well as those described below), to attach the filament to the drainage tube 72C, the end 68*b* of the filament 68 is attached to the forward extension portion 90 in order to draw the drainage tube 72C into and through the colon 70. Pulling of the end 68*a* of the filament 68 is continued until the forward extension portion 90 extends through the cecal wall 76 and the abdominal wall 48 and the filament 68 may then be removed.

Figure 16:
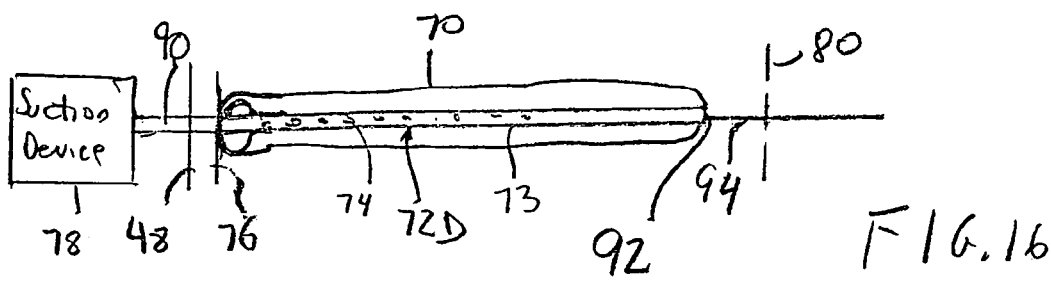
FIG. 16 is a schematic showing one embodiment of a fifth embodiment of drainage tube in accordance with the invention when used for colonic drainage and decompression.

A second embodiment which provides a forward flow through a drainage tube is shown in FIG. 16. In this embodiment, the main part 73 of drainage tube 72D includes a closed terminal end 92 and the drainage tube 72D has a rearward extention portion 94, which has no channel and may be filamentous, extending therefrom out of the patient's anus 80. When the drainage tube 72D is pulled through the colon 70 with the filament 68, the forward extension portion 90 of the drainage tube 72D is also passed through the colonic wall 76 and abdominal wall 48. The forward extension portion 90 of the drainage tube 72D is attached to the suction device 78 which applies suction through the drainage tube 72D. When the suction device 78 is operating, suction is applied from the forward end of the drainage tube 72D and causes fecal matter in the colon to be entrained by the suction force and drawn into the drainage tube 72D through the apertures 74 in the main part 73 and thus move in a forward direction through the drainage tube 72D out of the colon.

Since the distal end of the colon 70 and the rectum and anus do not allow air inflow, the suction force provided by the suction device 78 is applied intermittently, i.e., applied for a few moments, then turned off, then reapplied, turned off and so on. This embodiment of the drainage tube 72D can be removed by pulling it out through the anus by pulling on the rearward extension portion 94 which hangs out the anus 80.

The forward end of the drainage tube 72D is fixed in position by securing it to the skin, e.g., with suture, tape or a collar.

Figure 17:
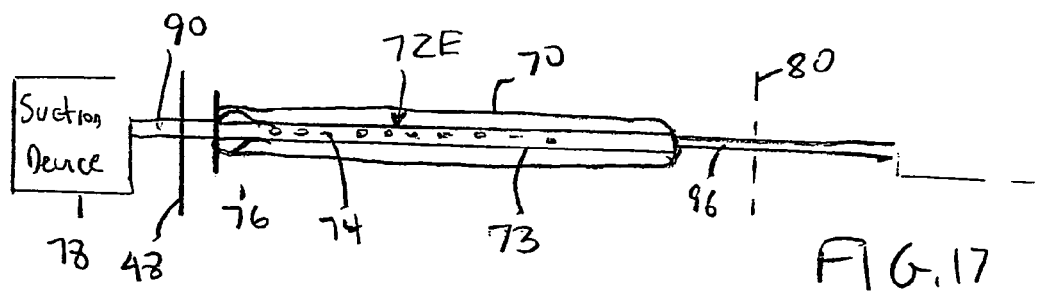
FIG. 17 is a schematic showing one embodiment of a sixth embodiment of a drainage tube in accordance with the invention when used for colonic drainage and decompression.

As shown in FIG. 17, it is also possible to use a drainage tube 72E which includes a rearward extension portion 96 at the rearward end of the main part 73 which defines an air inflow channel communicating with the lumen in the main part 73. The rearward extension portion 96 passes outside of the patient's body through the anus 80. The air inflow channel of the rearward extension portion 96 is open and communicates with the ambient atmosphere and prevents formation of a vacuum behind the fecal matter when suction is applied continuously by the suction device 78. This improves the function of the device and minimizes injury to the bowel mucosa. An air flow is created by the suction device 78 from the ambient atmosphere, through the air inflow channel and through the lumen of the main part 73 of the drainage tube 72E, which includes the apertures 74. Fecal matter is drawn into the drainage tube 72E through the apertures 74 by the suction force applied by the suction device 78 and sucked out of the colon 70 to a waste collection device associated with the suction device 78 (not shown).

The forward end of the drainage tube 72E is fixed in position by securing it to the skin, e.g., with suture, tape or a collar.

Figure 18:
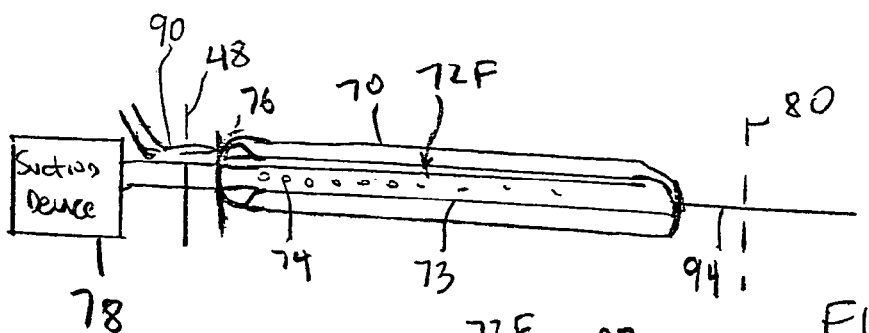
FIG. 18 is a schematic showing one embodiment of a seventh embodiment of a drainage tube in accordance with the invention when used for colonic drainage and decompression.
Figure 19:
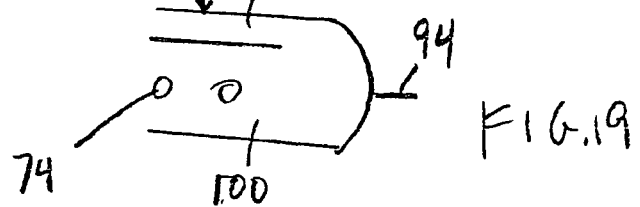
FIG. 19 is an enlarged view of the rearward end of the drainage tube shown in FIG. 18.

Another manner to introduce air into the drainage tube 72F is to construct a drainage tube 72F with a main part 73 having an air passage 102 alongside an effluent passage 100 in a similar manner as shown in FIGS. 13 and 14 but with the closed end of the drainage tube being at the rearward end of the drainage tube. This embodiment is shown in FIGS. 18 and 19 wherein the rearward end of the air passage 102 opens into the effluent passage 100 and the forward end of the air passage 102 is coupled to an air channel in a forward extension portion 90 of the drainage tube 72F which is open and communicates with the ambient atmosphere. The forward extension portion 90 also includes an effluent channel which communicates with the effluent passage 100 in the main part 73 and leads to the suction device 78. In this manner, it is possible to continuously apply suction since the formation of a vacuum behind the fecal matter is prevented. When suction is applied, an air flow would be formed from the ambient atmosphere, through the air channel in the forward extension portion 90, through the air passage 102 and then through the effluent passage 100 and through the effluent channel in the forward extension portion 90 to the suction device 78. Fecal matter is drawn into the drainage tube 72F through the apertures 74 in the drainage tube 72F and sucked out of the colon 70 to the waste collection device associated with the suction device 78.

The forward end of the drainage tube 72F is fixed in position by securing it to the skin, e.g., with suture, tape or a collar.

The first three described embodiments of the drainage tube in accordance with the invention, designated 72, 72A and 72B, all had a transition point where the main part 73 containing the apertures 74 transitions to a more forward section, either a filament (drainage tubes 72 and 72B) or a forward extension portion (drainage tube 72A), which has a smaller diameter than the main part 73. Therefore, all these drainage tubes 72, 72A, 72B can serve to hold the cecal wall 76 against the inner peritoneal lining of the abdominal wall 48 when the forward extension portion or filament, is pulled and fixed under slight tension to the skin. Such an arrangement serves to help prevent the escape of gas or fecal matter through the cecal wall alongside the drainage tube into the abdominal cavity. However, the embodiments of the drainage tube in accordance with the invention designated 72C, 72D, 72E and 72F (in FIGS. 15-19), by virtue of the fact that the forward and main parts have similar diameters, cannot press the cecal wall 76 against the abdominal wall 48. Therefore, it is advantageous to have a bulbous ring 84 at the most forward end of the main part 73 of the drainage tubes, forward of all apertures, which can serve to press the cecal wall 76 against the abdominal wall 48 when the forward section of the tubes 72C, 72D, 72E and 72F are fixed to the skin under slight tension. The bulbous ring 84 may have a generally spherical shape with a channel formed therein which receives a portion of the main part 73 of the drainage tube. The bulbous ring 84 is mounted and fixed over the drainage tube at the appropriate location. Another purpose served by the bulbous ring 84 is to serve as a stop and prevent the main part 73 and its apertures from being pulled out through the wall 76 of the cecum when the drainage tubes 72C, 72D, 72E and 72F are inserted, or at anytime thereafter. Alternatively, instead of a bulbous ring, there can be a bulbous expansion of the most forward end of the main part 73 of the drainage tube 72.

In colonic drainage and decompression, the application of suction via the suction device 78 continues as long as it is considered necessary to perform colonic drainage and decompression. When it is determined that colonic drainage and decompression is no longer needed the forward end of the drainage tube 72 is unfixed and the fixation device (e.g. suture, tape or a collar) is removed. The drainage tube 72 can then easily be pulled out of the colon 70 through the anus 80.

The description above has been based on the use of the device for colonic drainage and decompression. The same device, and method for using the same, are applicable to treatments and procedures in other body cavities, whether body cavities in humans or animals, in which it is desired to provide a tube extending through most or all of the cavity for the purpose of removing material from the cavity. Thus, the invention is not limited to colonic drainage and decompression devices and methods and encompasses any type of invasive body cavity treatments and procedures in which it is desired to remove material therefrom.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A method for inserting an apparatus into a bowel, comprising:
   inserting a guidewire into the bowel through an opening into the bowel; then
   passing a filament, unattached to the guidewire, from outside the bowel through the bowel wall into the bowel lumen and into initial engagement with the guidewire at a location in the bowel; then
   withdrawing the guidewire from the bowel through the opening into the bowel, after the filament is engaged with the guidewire, to thereby draw the filament through the bowel and out of the opening;
   attaching the apparatus to a portion of the filament after the guidewire and said portion of the filament have been withdrawn from the bowel; and
   drawing the filament with attached apparatus back through the opening into the bowel.

2. The method of claim 1, wherein the step of passing the filament through the bowel wall and into engagement with the guidewire comprises forming the guidewire with a through channel and passing the filament through the channel of the guidewire.

3. The method of claim 2, wherein the step of passing the filament through the bowel wall and into engagement with the guidewire further comprises forming the channel in a bulbous enlargement of the guidewire and passing a needle with the filament engaged therewith through the bowel wall and through the channel.

4. The method of claim 3, further comprising forming the bulbous enlargement with a diameter of about 0.25 inches to about 0.75 inches.

5. The method of claim 1, further comprising locating a bulbous enlargement of the guidewire in the bowel, the filament being passed through the bowel wall and into engagement with the bulbous enlargement.

6. The method of claim 1, wherein the step of attaching the filament to the apparatus comprises passing the filament through a tip of the apparatus and tying it around a wall of the apparatus.

7. The method of claim 1, wherein the step of attaching the apparatus to the filament comprises passing the filament through a tip of the apparatus and out a side hole thereof and then tying the filament to a filament button, and pulling on the filament so that the filament button returns to the interior of the apparatus and abuts against the inner surface of the tip of the apparatus, the filament button being dimensioned such that it is unable to pass back out through the tip of the apparatus thereby securing the filament to the apparatus.

8. The method of claim 1, further comprising fixing the apparatus in place in the bowel.

9. The method of claim 8, wherein the step of fixing the apparatus in place comprises cutting the filament to leave a portion connected to the apparatus, passing this portion of the filament through the abdominal wall and fixing this portion of the filament to the patient's skin.

10. The method of claim 8, wherein the step of fixing the apparatus in place comprises cutting the filament to leave a portion connected to the apparatus, passing this portion of the filament through the abdominal wall to an exterior of the body, winding the filament outside of the body onto a spool and fixing the spool on the body.

11. The method of claim 8, wherein the step of fixing the apparatus in place comprises passing a forward extension portion of the apparatus through bowel wall and the abdominal wall and securing the apparatus to the patient's skin.

12. The method of claim 11, further comprising securing the apparatus to the patient's skin with suture, tape or a collar.

13. The method of claim 1, wherein further comprising forming a structure on the guidewire which is adapted to enable the filament to be engaged therewith.

14. The method of claim 1, wherein the step of passing the filament through the bowel wall and into engagement with the guidewire comprises passing a needle with the filament engaged therewith, but unattached to the guidewire, through the bowel wall.

15. The method of claim 14, where the step of passing the filament through the bowel wall and into engagement with the guidewire comprises passing a needle with the filament engaged therewith, but unattached to the guidewire, through the bowel wall, through a channel in the guidewire, and through the bowel wall, so that the needle passes completely through the bowel.

16. The method of claim 15, further comprising holding the needle with the filament engaged therewith when withdrawing the guidewire from the bowel and out of the opening.

17. The method of claim 15, further comprising:
   severing the needle after the filament is engaged with the guidewire; and
   clamping a forward end of the filament before withdrawing the guidewire from the bowel and out of the opening.

18. The method of claim 15, further comprising:
   passing the needle through the abdominal wall and out of the body after the filament is engaged with the guidewire and the needle is passed out of the bowel; and then
   clamping a forward end of the filament outside of the body before withdrawing the guidewire from the bowel and out of the opening.

19. The method of claim 1, wherein the apparatus is a tubular apparatus.

20. The method of claim 1, wherein the apparatus is a drainage tube.

21. The method of claim 1, wherein the opening into the bowel is the anus.

22. A method for inserting an apparatus into a bowel, comprising:
   inserting a guidewire into the bowel through an opening into the bowel; then
   passing a filament through the bowel wall into the bowel lumen and into engagement with the guidewire;
   withdrawing the guidewire from the bowel and out of the opening, after the filament is engaged with the guidewire, to thereby draw the filament through the bowel and out of the opening;

attaching the apparatus to the filament after the guidewire and engaged filament have been withdrawn from the bowel; and drawing the filament with attached apparatus back through the opening into the bowel;

the step of attaching the apparatus to the filament comprising passing the filament through a tip of the apparatus and out a side hole thereof and then tying the filament to a filament button, and pulling on the filament so that the filament button returns to the interior of the apparatus and abuts against the inner surface of the tip of the apparatus, the filament button being dimensioned such that it is unable to pass back out through the tip of the apparatus thereby securing the filament to the apparatus.

23. A method for inserting an apparatus into a bowel, comprising:

inserting a forward end of a guidewire into the bowel through an opening into the bowel; then passing the forward end of the guidewire to a second location in the bowel; then without the forward end of the guidewire exiting the bowel, passing a filament through the bowel wall into the bowel lumen and then bringing the filament and forward end of the guidewire into engagement with one another at the second location in the bowel;

withdrawing the guidewire from the bowel through the opening into the bowel, after the filament is engaged with the guidewire, to thereby draw the second end of the filament through the bowel and out of the opening;

attaching the apparatus to the filament in the vicinity of the second end of the filament after the guidewire and a portion of the engaged filament have been withdrawn from the bowel;

drawing the filament with attached apparatus back through the opening in the bowel and through the bowel.

24. The method of claim 23, wherein the opening into the bowel is a natural orifice.

25. The method of claim 23, wherein the opening into the bowel is the anus.

26. The method of claim 23, wherein the apparatus is a tube.

27. The method of claim 23, wherein the apparatus is a drainage tube having apertures.

28. The method of claim 23, wherein the step of passing the filament through the bowel wall and into engagement with the guidewire comprises forming the guidewire with a through channel and passing the filament through the channel of the guidewire.

29. The method of claim 28, wherein the step of passing the filament through the bowel wall and into engagement with the guidewire further comprises forming the channel in a bulbous enlargement of the guidewire, and passing a needle with threaded filament through the bowel wall and through the channel.

30. The method of claim 29, further comprising forming the bulbous enlargement with a diameter of about 0.25 inches to about 0.75 inches.

31. The method of claim 23, further comprising locating a bulbous enlargement of the guidewire in the bowel, the filament being passed through the bowel wall and into engagement with the bulbous enlargement.

32. The method of claim 23, wherein further comprising forming a structure on the guidewire which is adapted to enable the filament to be engaged therewith.

33. The method of claim 23, wherein the step of passing the filament through the bowel wall and into engagement with the guidewire comprises passing a needle with the filament engaged therewith, but unattached to the guidewire, through the bowel wall.

34. The method of claim 33, further comprising holding the needle with the filament engaged therewith when withdrawing the guidewire from the bowel and out of the opening.

35. The method of claim 33, further comprising:

severing the needle after the filament is engaged with the guidewire; and clamping a forward end of the filament before withdrawing the guidewire from the bowel and out of the opening.

36. The method of claim 33, further comprising:

passing the needle from the inside of the bowel out of the body after the filament is engaged with the guidewire; and then clamping a forward end of the filament outside of the body before withdrawing the guidewire from the bowel and out of the opening.

37. The method of claim 23, wherein the step of attaching the filament to the apparatus comprises passing the filament through a tip of the apparatus and tying it around a wall of the apparatus.

38. The method of claim 23, further comprising fixing the apparatus in place in the bowel.

39. The method of claim 38, wherein the step of fixing the apparatus in place comprises cutting the filament to leave a portion connected to the apparatus, passing this portion of the filament through the abdominal wall and fixing this portion of the filament to the patient's skin.

40. The method of claim 38, wherein the step of fixing the apparatus in place comprises cutting the filament to leave a portion connected to the apparatus, passing this portion of the filament through the abdominal wall to an exterior of the body, winding the filament outside of the body onto a spool and fixing the spool on the body.

41. The method of claim 38, wherein the step of fixing the apparatus in place comprises passing a forward extension portion of the apparatus through bowel wall and the abdominal wall and securing the apparatus to the patient'skin.

42. The method of claim 41, further comprising securing the apparatus to the patient's skin with suture, tape or a collar.

* * * * *